United States Patent [19]

Rodewald

[11] Patent Number: 4,465,886

[45] Date of Patent: * Aug. 14, 1984

[54] SILICA-MODIFIED CATALYST AND USE FOR SELECTIVE PRODUCTION OF PARA-DIALKYL SUBSTITUTED BENZENES

[75] Inventor: Paul G. Rodewald, Rocky Hill, N.J.

[73] Assignee: Mobil Oil Corporation, New York, N.Y.

[*] Notice: The portion of the term of this patent subsequent to Nov. 28, 1995 has been disclaimed.

[21] Appl. No.: 502,868

[22] Filed: Jun. 9, 1983

[51] Int. Cl.$^3$ .......................... C07C 3/52; C07C 3/62
[52] U.S. Cl. .................................... 585/467; 585/475
[58] Field of Search .............................. 585/467, 475

[56] References Cited

U.S. PATENT DOCUMENTS 4,127,616  11/1978  Rodewald .......................... 585/467

*Primary Examiner*—Curtis R. Davis
*Attorney, Agent, or Firm*—Alexander J. McKillop; Michael G. Gilman; Dennis P. Santini

[57] ABSTRACT

The present invention relates to selective conversion of certain hydrocarbon feedstocks to product rich in para-dialkyl substituent benzenes over a catalyst composition comprising a crystalline zeolite having deposited thereon a coating of silica which extensively covers and resides substantially exclusively on the external surface thereof.

20 Claims, No Drawings

SILICA-MODIFIED CATALYST AND USE FOR SELECTIVE PRODUCTION OF PARA-DIALKYL SUBSTITUTED BENZENES

BACKGROUND OF THE INVENTION

1. Field of the Invention

This invention relates to a catalyst suitable for the selective production of para-dialkyl substituted benzenes and to a process for converting specified chargestocks to a high yield of para-dialkyl substituted benzenes utilizing such catalyst.

2. Description of the Prior Art

The disproportionation of aromatic hydrocarbons in the presence of zeolite catalysts has been described by Grandio et al. in the Oil and Gas Journal, Vol. 69, No. 48 (1971). U.S. Pat. Nos. 3,126,422; 3,413,374; 3,598,878; 3,598,879 and 3,607,961 show vapor-phase disporportionation of toluene over various catalysts.

In these prior art processes, the xylene product produced has the equilibrium composition of approximately 24 percent para, 54 percent meta and 22 percent ortho.

In addition to the above patents, other related prior art includes U.S. Pat. No. 2,904,607 which refers to alkylation of aromatic hydrocarbons with an olefin in the presence of a crystalline metallic aluminosilicate having uniform pore openings of about 6 to 15 Angstrom units. U.S. Pat. No. 3,251,897 describes alkylation of aromatic hydrocarbons in the presence of X- or Y-type crystalline aluminosilicate zeolites, specifically such type zeolites wherein the cation is rare earth and/or hydrogen. U.S. Pat. Nos. 3,751,504 and 3,751,506 describes vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273-280 (1970). The workers reported selective production of paraxylene over the approximate temperature range of 200° to 275° C., with the maximum yield of para-xylene in the mixture of xylenes, i.e. about 50 percent of the xylene product mixture being observed at 225° C. Higher temperatures were reported to result in an increase in the yield of meta-xylene and a decrease in the production of para and ortho-xylenes. U.S. Pat. No. 3,965,210 describes alkylation of toluene with methanol in the presence of a crystalline aluminosilicate zeolite, such as ZSM-5, which has been modified by contact with a polymer made up of meta-carborane units connected by siloxane units to selectively yield para-xylene. These latter catalysts have, however, suffered from the serious deficiency of loss of selectivity upon air regeneration. This is attributable to breakage of carbon-silicon bonds upon exposure to the high temperature of regeneration giving rise to isolated clusters of silica on the zeolite surface rather than the extensive surface coverage afforded by the technique described herein.

U.S. Pat. No. 2,722,504 describes a catalyst of an activated oxide such as silica gel having a thin layer of a silicone polymer deposited thereon to increase the organophilic character of the contact surface and, as such, seeks to avoid silica deposition.

Crystalline aluminosilicate zeolites, modified by reaction with an organic substituted silane, have been described in U.S. Pat. Nos. 3,682,996 and 3,698,157. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 type crystalline aluminosilicate zeolites modified by treatment with an organic-radical substituted silane are described, together with the use of such modified zeolites in chromatographic separation of the compounds in a $C_8$ aromatic feed stock.

U.S. Pat. No. 4,145,315 discloses a method for the production of silica modified zeolite catalysts which are prepared by contacting the specific zeolite with an organic solvent solution such as hexane, of a silicone fluid, distillation of the hexane, and air calcination of the zeolite residue.

Silica-modified catalysts are shown in U.S. Pat. Nos. 4,379,761; 4,100,219 and 4,090,981. In each instance the silica modification results from interaction of the zeolite portion of the catalyst with an organic solution comprising a silica source such as a silicone.

U.S. Pat. No. 4,088,605 shows altering a crystallization medium to substantially eliminate aluminum during crystallization in order to synthesize a zeolite with a coating of silica.

While the above-noted art is considered of interest in connection with the subject matter of the present invention, the catalyst, its method of manufacture and the conversion process described herein with that catalyst have not, insofar as is known, been heretofore described.

Of the xylene isomers, i.e. ortho, meta and para-xylene, meta-xylene is the least desired product, with para-xylene being the most desired product. Para-xylene is of particular value being useful in the manufacture of terephthalic acid which is an intermediate in the manufacture of synthetic fibers, such as "Dacron". Mixtures of xylene isomers, either alone or in further admixture with ethylbenzene, generally containing a concentration of about 24 weight percent para-xylene in the equilibrium mixture, have previously been separated by expensive superfractionation and multistage refrigeration steps. Such process, as will be realized, has involved high operation costs and has a limited yield.

SUMMARY OF THE INVENTION

In accordance with the present invention, there has been discovered a method for preparing a catalyst which is particularly applicable for the selective production of para-dialkyl substituted benzenes. The catalyst comprises a porous crystalline aluminosilicate zeolite having deposited thereon a coating of silica extensively covering the surface of said zeolite. The coating of silica is substantially exclusively on the external surface of the zeolite as a result of contact of the latter with an aqueous emulsion or dispersion of a silicone compound of a molecular size incapable of entering the pores thereof, followed by heating in an oxygen-containing atmosphere, such as air, to a temperature in excess of 300° C. but below a temperature at which crystallinity of the zeolite is adversely affected at a rate such that the silicone compound does not volatilize prior to undergoing oxidation to silica. The zeolite employed has an activity, in terms of alpha value, of between about 2 and about 5000, a xylene sorption capacity greater than 1 gram/100 grams of zeolite and an ortho-xylene sorption time, hereinafter described, for 30 percent of such capacity of greater than 10 minutes, the sorption capacity and sorption time being measured at 120° C. and a xylene pressure of 4.5±0.8 mm. of mercury. The resulting catalyst has been found to possess a long catalytic life, e.g. to be capable of regeneration after catalytic use without substanial loss in activity.

The above catalyst has been found to be particularly useful in the selective production of para-dialkyl substituted benzenes containing alkyl groups of 1 to 4 carbon atoms, such as para-xylene, by conversion in the presence thereof, of a hydrocarbon precursor such as a mono alkyl-substituted benzene having 1-4 carbon atoms in the alkyl substituent or a mixture of such precursor or benzene with an alkylating agent containing from 1 to 4 carbon atoms. Typical of the above conversion processes are the disproportionation of toluene and the alkylation of benzene or toluene with a methylating agent, e.g. methanol.

In a preferred embodiment, the catalyst prepared by the present method is used in a process which comprises conversion of the specified precursor reactants to yield xylenes in which the proportion of para-xylene is substantially in excess of the normal equilibrium concentration and preferably in excess of 30 weight percent of the xylene product produced in the presence of the specified catalyst at a temperature between about 250° C. and about 750° C. and a pressure between about 0.1 and about 100 atmospheres, utilizing a feed weight hourly space velocity (WHSV) between about 0.1 and about 2000. The latter WHSV is based upon the weight of catalyst composition, i.e. total weight of active catalyst and binder therefor. The effluent is separated and distilled to remove the desired product, e.g. para-xylene, and unreacted material is recycled for further reaction.

DESCRIPTION OF SPECIFIED EMBODIMENTS

The zeolite base component of the present catalyst upon which silica deposition is effected is characterized by particular activity and sorption properties. Thus, the porous crystalline aluminosilicate zeolite employed herein necessarily has: (1) an activity, in terms of alpha value, of between about 2 and about 5000, (2) a xylene sorption capacity greater than 1 gram/100 grams of zeolite and (3) an ortho-xylene sorption time for 30 percent of said capacity of greater than 10 minutes, where the sorption capacity and sorption time are measured at 120° C. and a xylene pressure of 4.5±0.8 mm. of mercury.

The alpha value reflects the relative activity of the catalyst with respect to a high activity silica-alumina cracking catalyst. To determine the alpha value as such term is used herein, n-hexane conversion is determined at about 538° C. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 538° C. Catalytic activity of the catalysts are expressed as multiple of this standard, i.e. the silica-alumina standard. The silica-alumina reference catalyst contains about 10 weight percent $Al_2O_3$ and remainder $SiO_2$. This method of determining alpha, modified as described above, is more fully described in the Journal of Catalysis, Vol. VI, Pages 278–287, 1966, as well as U.S. Pat. No. 3,354,078, incorporated herein by reference as to that description.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5±0.8 mm of mercury and an orthoxylene sorption time for 30 percent of said capacity of greater than 10 minutes (at the same conditions of temperature and pressure) are required in order to achieve the desired selective production of para-dialkyl substituted benzenes.

It has been found that zeolites exhibiting very high selectivity for para-dialkylbenzene production require a very long time up to and exceeding a thousand minutes to sorb o-xylene in an amount of 30% of total xylene sorption capacity. For those materials it is more convenient to determine the sorption time for a lower extent of sorption, such as 5%, 10%, or 20% of capacity, and to estimate the 30% sorption time by applying the following multiplication factors F as illustrated for 5% sorption:

| $t_{0.3} = F \cdot t_{0.05}$ Percent of sorption capacity | Factor (F) to Estimate 30% Sorption Time |
| --- | --- |
| 5 | 36 |
| 10 | 9 |
| 20 | 2.2 |

Zeolites such as zeolite X, zeolite Y, ZSM-4, faujasite, mordenite, ferrierite and offretite which satisfy the aforenoted activity and sorption characteristics are within the confines of this invention. Particularly preferred are those zeolites having a silica to alumina ratio of at least about 12 and a constraint index within the approximate range of 1 to 12. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly the preferred type zeolites useful in this invention possess, in combination: a silica to alumina mole ratio of at least about 12; and a structure providing constrained access to the crystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites after activation, acquire an intracrystalline sorption capacity for normal hexane which is greater than that for water, i.e. they exhibit "hydrophobic" properties. This hydrophobicity property would indicate that a suitable medium for the silicon compound used herein should be organic, eg. n-hexane, benzene, toluene, chloroform, etc. and not water, If an organic medium is used, the silicon compound would be dissolved therein and the hydrophobic properties of the zeolite would not work against deposition of the silicon compound on the zeolite. However, it has been surprisingly found than an aqueous emulsion of a silicon-containing compound is useful for this purpose.

The economic advantages accompanying the present method for catalyst-preparation when compared to preparing such a catalyst via contact with an organic solution of a silicon compound are numerous. Water vapor can be vented to the atmosphere while organic vapor can not. The use of water in place of organic solvent, when a "suitable solvent" as required by the prior art for "dissolving" a particular compound which is not soluble in water, is not so readily apparent an economic advantage. Clearly, and unexpectedly, the use of a water emulsion in place of an organic solvent in treatment of a hydrophobic crystalline zeolite to produce even an equivalent product is an advantage which would not be readily apparent.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of course sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| Zeolite | CI |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 1.5 |
| ZSM-4 | 0.5 |
| H—Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. . Likewise, other variables such as the crystal size of the zeolite, the presence of possible occluded contaminants and binders intimately combined with the zeolite may affect the constraint index. It will accordingly be understood by those skilled in the art that the constraint index, as utilized herein,, while affording a highly useful means for characterizing the zeolites of interest in approximate, taking into consideration the manner of its determination, with probability, in some instances of compounding variable extremes. However, in all instances, at a temperature within the above-specified range of 550° F. to 950° F., the constraint index will have a value for any given zeolite of interest herein within the approximate range of 1 to 12.

The latter class of zeolites defined as useful herein include ZSM-5, ZSM-5/ZSM-11 intermediate, ZSM-11, ZSM-12, ZSM-23, ZSM-35, ZSM-38, ZSM-48 and other similar materials.

ZSM-5 is described in greater detail in U.S. Pat. Nos. 3,702,886 and Re. 29,948. The entire descriptions contained within those patents are incorporated herein by reference.

ZSM-5/ZSM-11 intermediate is described in U.S. Pat. No. 4,229,424, l the entire contents of which is incorporated herein by reference.

ZSM-11 is described in U.S. Pat. No. 3,709,979. That description is incorporated in its entirety herein by reference.

ZSM-12 is described in U.S. Pat. No. 3,832,449. That entire description is incorporated herein by reference.

ZSM-23 is described in U.S. Pat. No. 4,076,842. The entire content thereof is incorporated herein by reference.

ZSM-35 is described in U.S. Pat. No. 4,016,245. The description of that zeolite, in its entirety, is incorporated herein by reference.

ZSM-38 is more particularly described in U.S. Pat. No. 4,046,859, the entire description of which is incorporated herein by reference.

ZSM-48 is described in U.S. Pat. No. 4,375,573 and its entire description of ZSM-48 is incorporated herein by reference.

It is to be understood that by incorporating by reference the foregoing patents to describe examples of specific members of the novel class with greater particularly, it is intended that identification of the therein disclosed crystalline zeolites by resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .50 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight, and often to less than about 0.5 percent by weight, may be used. Thus, the original alkali metal of the zeolite may be replaced by ion exchange with other suitable ions of Groups IB to VIII of the Periodic Table, including, by way of example, nickel, copper, zinc, palladium, platinum, calcium or rare earth metals.

In practicing the desired selective conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silicaalumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

In accordance with this invention, a porous crystalline aluminosilicate zeolite, as above characterized, has a coating of silica deposited thereon. Such coating extensively covers the external surface of the zeolite and resides substantially completely on the external surface. The coating of silica is deposited on the surface of the zeolite by contacting the latter with an aqueous emulsion of a silicone compound having a molecular size incapable of entering the pores of the zeolite and subsequently heating in an oxygen-containing atmosphere, such as air, to a temperature above 300° C. but below a temperature at which the crystallinity of the zeolite is adversely affected at a rate such that the silicone compound does not volatize before undergoing oxidation of silica.

The silicone compound utilized to effect the silica coating is characterized by the general formula:

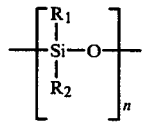

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, other than hydrogen and other than methyl if $R_1$ is hydrogen and n is an integer of at least 10 and generally in the range of 10 to 1000. The molecular weight of the silicone compound employed is generally between about 500 and about 20,000 and preferably within the approximate range of 1000 to 10,000. Representative silicone compounds include dimethylsilicone, diethylsilicone, phenylmethylsilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone.

The aqueous emulsion of the silicone compound is contacted with the above described zeolite at a temperature between about 10° C. and about 200° C. for a period of time sufficient to deposit the ultimately desired amount of silicone thereon. Time of contact will generally be within the range of 0.2 to 5 hours, during which time the mixture is desirably subjected to evaporation. The resulting residue is then calcined in an oxygen-containing atmosphere, preferably air, at a rate of 0.2° to 5° C./minute to a temperature greater than 300° C. but below a temperature at which the crystallinity of the zeolite is adversely affected. Generally, such temperature will be below 700° C. Preferably the temperature of calcination is within the approximate range of about 350° C. to about 550° C. The product is maintained at the calcination temperature usually for 1 to 24 hours to yield a silica-coated zeolite containing between about 0.5 and about 30 weight percent and preferably between about 1 and 15 weight percent silica.

The charge stock used herein for the selective production of para-dialkyl substituted benzenes containing alkyl groups of 1 to 4 carbon atoms by contact, under conversion conditions, with the above-described catalyst includes a hydrocarbon precursor selected from the group consisting of monoalkyl-substituted benzenes having 1-4 carbon atoms in the alkyl substituent, such as toluene, ethyl benzene, propyl benzene or butyl benzene and a mixture of such precursor or benzene with an alkylating agent containing from 1 to 4 carbon atoms.

Typical of the processes contemplated herein are disproportionation of toluene to benzene and xylene, wherein the proportion of para-xylene obtained is greatly in excess of its normal equilibrium concentration. Such process is effectively carried out at a temperature of between about 400° C. and about 700° C. at a pressure between about 1 atmosphere and about 100 atmospheres utilizing a weight hourly space velocity of between about 1 and about 50.

The use of mixed aromatics as feed is also feasible. For example, a mixture of ethylbenzene and toluene is converted selectively to a mixture rich in para-dialkyl substituted benzene such as p-diethylbenzene and p-ethyltoluene, the latter predominating at high toluene to ethylbenzene ratios in the feed.

Reaction of feedstock benzene, toluene, ethylbenzene, propylbenzene or butylbenzene with an alkylating agent containing from 1 to 4 carbon atoms is also contemplated using the catalyst described hereinabove. Products of this reaction include mixtures rich in para-dialkyl substituted benzenes. Suitable alkylating agents include olefins, alcohols, alkyl halides, ethers and sulfides having from 1 to 4 carbon atoms. Reprsentative of such compounds are ethylene, propylene, butylene, methanol, ethanol, propanol, butanol, methyl chloride, ethyl chloride, propyl chloride, butyl chloride, dimethylether, dimethylsulfide, diethlether, diethylsulfide, dipropylether, dipropylsulfide, dibutylether, and dibutylsulfide. Alkylation is suitably carried out at a temperature between about 250° C. and about 700° C. at a pressure between about 1 atmosphere and about 100 atmospheres employing a weight hourly space velocity of between about 0.1 and about 200. The mole ratio of feedstock/alkylating agent may be from about 1/1 to about 20/1 for this reaction.

It is contemplated that the conversion process described herein may be carried out as a batch type, semi-continuous or continuous operation utilizing a fixed or moving bed catalyst system. The catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the charge stock. With use of the present silica-coated zeolite catalyst, regeneration has been found to restore the activity of the catalyst to a high level, thereby providing a long catalyst life. It is particularly feasible to conduct the desired conversion in the presence of hydrogen utilizing a hydrogen/hydrocarbon mole ratio of between about 2 and about 20, with hydrogen pressure extending from 1 atmosphere up to 100 atmospheres. The presence of hydrogen in the reaction zone has been found to very substantially reduce the aging rate of the catalyst.

While the above process has been described with reference to selective production of para-dimethyl substituted benzenes, typified by para-xylene, it is contemplated that other para-dialkyl substituted benzenes, wherein the alkyl group contains from 1 to 4 carbon atoms may similarly be selectively produced. Thus, utilizing the technique described herein, it is contempltated that with selection of suitable precursor, a mixture of ethyl benzene and toluene may be selectively converted to para-ethyl toluene; ethyl benzene may be selectively converted to diethyl benzene, propyl benzene may be converted to dipropyl benzene and butyl benzene may be selectively converted to dibutylbenzenes.

The following examples will serve to illustrate the process and catalyst of the present invention without limiting the same.

EXAMPLE 1

To 2.0 grams of NH₄ZSM-5 of 1-2 micron crystal size was added 0.45 gram phenylmethylsilicone as a 9% emulsion in water. After distillation of the water the residue was program air-calcined at 1° C./minute and then 7 hours at 538° C. The resulting catalyst contained a nominal 9% extracrystalline silica.

EXAMPLE 2

A sample of extracrystalline silica-modified HZSM-5 prepared as in Example 1 was tested in a flow reactor for toluene disproportionation at 482° C., 6.5 WHSV, 400 psig, and a hydrogen/toluene mole ratio of 4.0. The results are shown in Table I below and are compared to data from an intracrystalline-modified HZSM-5 catalyst prepared as in Example 1 but using an aqueous emulsion of methylhydrogensilicone which can penetrate the pores of ZSM-5. The intracrystalline-modified HZSM-5 had 13% intracrystalline silica.

TABLE I

| | Wt. % of Product Xylenes | | |
|---|---|---|---|
| | p-Xylene | m-Xylene | o-Xylene |
| Thermodynamic Equilibrium | 24 | 52 | 24 |
| 13% Intracrystalline Silica | 25 | 52 | 23 |
| 9% Extracrystalline Silica | 35 | 48 | 17 |

The above results show a 45.8 percent increase in the valuable para-xylene isomer when compared to expected thermodynamic equilibrium results. The extracrystalline-modified catalyst of the present invention also provided an improvement over the same process conducted over an intracrystalline-modified catalyst of 40 percent. The process conducted with the catalyst of the present invention further provided a reduced meta-isomer, the least desirable of the xylene isomers.

EXAMPLE 3

Alkylation of toluene with methanol is carried out using the extracrystalline silica-modified HZSM-5 prepared as in Example 1. Operating temperatures are varied through the range of 400°-550° C., while maintaining 10 WHSV, atmospheric pressure, a toluene/methanol mole ratio of 4.0, and a hydrogen/toluene mole ratio of 2.0. Table II summarizes the results.

TABLE II

| Temperature °C. | Wt. % p-Xylene in Product Xylenes |
|---|---|
| 550 | 88 |
| 500 | 91 |
| 450 | 94 |

TABLE II-continued

| Temperature °C. | Wt. % p-Xylene in Product Xylenes |
|---|---|
| 400 | 95 |

EXAMPLE 4

Alkylation of toluene with ethylene is carried out using the extracrystalline silica-modified HZSM-5 prepared as in Example 1. Operating temperatures are varied through the range of 400°-425° C. while maintaining 29 WHSV (toluene), 100 psig, and a toluene/ethylene/hydrogen mole ratio of 8/1/3. Table III summarizes the results.

TABLE III

| Temperature °C. | Wt. % p-Ethyltoluene in Product Ethyltoluenes |
|---|---|
| 400 | 91 |
| 425 | 94 |

It should be recognized that the advantages for catalyst preparation in accordance with the present invention include the fact that an aqueous emulsion of the silicone fluid may be substituted for an organic solution thereof in the preparation of the catalyst with economic advantages that on a commercial scale are quite significant. Additionally, it will be noted that as hereinbefore described the process water used in the silicone emulsion may be vented to the atmosphere whereas organic solvents such as hexane may not and must be condensed to avoid hydrocarbon emissions.

What is claimed is:

1. A conversion process which comprises contacting a feedstock selected from the group consisting of toluene, ethylbenzene, propylbenzene, butylbenzene and mixtures thereof, at conversion conditions including a temperature of from about 250° C. to about 750° C., a pressure of from about 0.1 atmosphere to about 100 atmospheres and a feedstock weight hourly space velocity of from about 0.1 to about 2000, with catalyst composition comprising a crystalline zeolite having deposited thereon a coating of silica which extensively covers and resides substantially exclusively on the external surface thereof as a result of contact of a crystalline zeolite, having hydrophobic properties after heating same at 540° C. for one hour in an inert atmosphere, with an aqueous emulsion of a silicon-containing compound of a molecular size substantially incapable of entering the pores of the zeolite at a temperature of from about 10° C. to about 200° C. for a time sufficient to permit from about 0.5 weight percent to about 30 weight percent silica to be deposited on the crystalline zeolite upon heating in an oxygen-containing atmosphere at a temperature of from 300° C. to about 700° C., said silicon-containing compound having the general formula:

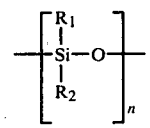

where R₁ is hydrogen, fluorine, hydroxy, alkyl, aralkyl, alkaryl, or fluoro-alkyl, the hydrocarbon substituents containing from 1 to 10 carbon atoms, $R_2$ is selected from the same group as $R_1$, other than hydrogen and other than methyl if $R_1$ is hydrogen, and n is an integer of at least 10, said crystalline zeolite being characterized by an activity, in terms of alpha value, of between about 2 and about 5000, a xylene sorption capacity greater than 1 gram/100 grams of zeolite and an ortho-xylene sorptin time for 30 percent of said capacity greater than 10 minutes, said sorption capacity and sorption time being measured at 120° C. and a pressure of 4.5±0.8 mm. of mercury, and recovering a resulting product comprising dialkyl substituted benzenes wherein the amount of para-isomer thereof is in excess of normal equilibrium concentration.

2. The process of claim 1 wherein the feedstock comprises toluene, the conversion conditions include a temperature of from about 400° C. to about 700° C., a pressure of from about 1 atmosphere to about 100 atmospheres and a toluene weight hourly space velocity of from about 1 to about 50, and said product comprises benzene and xylenes, the concentration of product para-xylene being in excess of normal equilibrium concentration relative to product meta-xylene and product ortho-xylene.

3. The process of claim 1 wherein said feedstock comprises ethylbenzene and toluene and said product comprises para-diethylbenzene and para-ethyltoluene.

4. The process of claim 1 wherein said crystalline zeolite is further characterized by a silia/alumina mole ratio of at least about 12, and a constraint index within the approximate range of 1 to 12.

5. The process of claim 4 wherein said crystalline zeolite has the structure of ZSM-5, ZSM-5/ZSM-11 intermediate, ZSM-11, ZSM-12, ZSM-23, ZSM-35, ZSM-38 or ZSM-48.

6. The process of claim 5 wherein said crystalline zeolite has the structure of ZSM-5.

7. The process of claim 1 wherein said silicon-containing compound is selected from the group consisting of dimethylsilicone, diethylsilicone, phenylmethylsilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone.

8. The process of claim 7 wherein said silicon-containing compound is phenylmethylsilicone or dimethylsilicone.

9. A conversion process which comprises contacting a feedstock comprising benzene with an alkylating agent selected from the group consisting of alcohols, olefins, alkylhalides, ethers and sulfides, said alkylating agent having from 1 to 4 carbon atoms, in the presence of a catalyst composition at conversion conditions including a temperature of from about 250° C. to about 700° C., a pressure of from about 1 atmosphere to about 100 atmospheres and a weight hourly space velocity of from about 0.1 to about 200, said catalyst composition comprising a crystalline zeolite having deposited thereon a coating of silica which extensively covers and resides substantially exclusively on the external surface thereof as a result of contact of a crystalline zeolite, having hydrophobic properties after heating same at 540° C. for one hour in an inert atmosphere, with an aqueous emulsion of a silicon-containing compound of a molecular size substantially incapable of entering the pores of the zeolite at a temperature of from about 10° C. to about 200° C. for a time sufficient to permit from about 0.5 weight percent to about 30 weight percent silica to be deposited on the crystalline zeolite upon heating in an oxygen-containing atmosphere at a temperature of from 300° C. to about 700° C., said silicon-containing compound having the general formula:

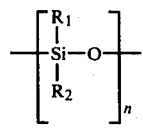

wherein $R_1$ is hydrogen, fluorine, hydroxy, alkyl, aralkyl, alkaryl, or fluoro-alkyl, the hydrocarbon substituents containing from 1 to 10 carbon atoms, $R_2$ is selected from the same group as $R_1$, other than hydrogen and other than methyl if $R_1$ is hydrogen, and n is an integer of at least 10, said crystalline zeolite being characterized by an activity, in terms of alpha value, of between about 2 and about 5000, a xylene sorption capacity greater than 1 gram/100 grams of zeolite and an ortho-xylene sorption time for 30 percent of said capacity greater than 10 minutes, said sorption capacity and sorption time being measured at 120° C. and a pressure of 4.5±0.8 mm. of mercury, and recovering a resulting product comprising para-dialkyl substituted benzenes.

10. The process of claim 9 wherein said crystalline zeolite is further characterized by a silica/alumina mole ratio of at least about 12, and a constraint index within the approximate range of 1 to 12.

11. The process of claim 10 wherein said crystalline zeolite has the structure of ZSM-5, ZSM-5/ZSM-11 intermediate, ZSM-11, ZSM-12, ZSM-23, ZSM-35, ZSM-38 or ZSM-48.

12. The process of claim 11 wherein said crystalline zeolite has the structure of ZSM-5.

13. The process of claim 9 wherein said silicon-containing compound is selected from the group consisting of dimethylsilicone, diethylsilicone, phenylmethylsilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone.

14. The process of claim 13 wherein said silicon-containing compound is phenylmethylsilicone or dimethylsilicone.

15. A conversion process which comprises contacting a feedstock selected from the group consisting of toluene, ethylbenzene, propylbenzene, butylbenzene and mixtures thereof with an alkylating agent selected from the group consisting of alcohols, olefins, alkylhalides, ethers and sulfides, said alkylating agent having from 1 to 4 carbon atoms, in the presence of a catalyst composition, at conversion conditions including a temperature of from about 250° C. to about 700° C., a pressure of from about 1 atmosphere to about 100 atmospheres and a weight hourly space velocity of from about 0.1 to about 200, said catalyst composition comprising a crystalline zeolite having deposited thereon a coating of silica which extensively covers and resides substantially exclusively on the external surface thereof as a result of contact of a crystalline zeolite, having hydrophobic properties after heating same at 540° C. for one hour in an inert atmosphere, with an aqueous emulsion of a silicon-containing compound of a molecular size substantially incapable of entering the pores of the zeolite at a temperature of from about 10° C. to about 200° C. for a time sufficient to permit from about 0.5 weight percent to about 30 weight percent silica to be deposited on the crystalline zeolite upon heating in an oxygen-containing atmosphere, at a temperature of from about 300° C. to about 700° C., said silicon-containing compound having the general formula:

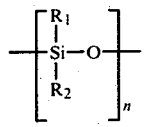

wherein R is hydrogen, fluorine, hydroxy, alkyl, aralkyl, alkaryl, or fluoro-alkyl, the hydrocarbon substituents containing from 1 to 10 carbon atoms, $R_2$ is selected from the same group as $R_1$, other than hydrogen and other than methyl if $R_1$ is hydrogen, and n is an integer of at least 10, said crystalline zeolite being characterized by an activity, in terms of alpha value, of between about 2 and about 5000, a xylene sorption capacity greater than 1 gram/100 grams of zeolite and an ortho-xylene sorption time for 30 percent of said capacity greater than 10 minutes, said sorption capacity and sorption time being measured at 120° C. and a pressure of 4.5±0.8 mm. of mercury, and recovering a resulting product comprising para-dialkyl substituted benzenes.

16. The process of claim 15 wherein said crystalline zeolite is further characterized by a silica/alumina mole ratio of at least about 12, and a constraint index within the approximate range of 1 to 12.

17. The process of claim 16 wherein said crystalline zeolite has the structure of ZSM-5, ZSM-5/ZSM-11 intermediate, ZSM-11, ZSM-12, ZSM-23, ZSM-35, ZSM-38 or ZSM-48.

18. The process of claim 17 wherein said crystalline zeolite has the structure of ZSM-5.

19. The process of claim 15 wherein said silicon-containing compound is selected from the group consisting of dimethylsilicone, diethylsilicone, phenylmethylsilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone.

20. The process of claim 19 wherein said silicon-containing compound is phenylmethylsilicone or dimethylsilicone.

* * * * *